(12) United States Patent
Xu et al.

(10) Patent No.: US 11,660,120 B2
(45) Date of Patent: May 30, 2023

(54) VISUALIZED SURGICAL ASSEMBLY AND CORRESPONDING ENDOSCOPE THEREOF

(71) Applicant: SHANGHAI OUTAI MEDICAL EQUIPMENT CO. LTD., Shanghai (CN)

(72) Inventors: Rui Xu, Shanghai (CN); Suping Liu, Shanghai (CN); Zhujun Tang, Shanghai (CN); Tong Zhao, Shanghai (CN); Lei Cen, Shanghai (CN); Yungui Liu, Shanghai (CN); Xukai Wang, Shanghai (CN); Qiang Cheng, Shanghai (CN)

(73) Assignee: SHANGHAI OUTAI MEDICAL EQUIPMENT CO., LTD., Shanghai (CN)

( * ) Notice: Subject to any disclaimer, the term of this patent is extended or adjusted under 35 U.S.C. 154(b) by 95 days.

(21) Appl. No.: 17/423,532

(22) PCT Filed: May 13, 2019

(86) PCT No.: PCT/CN2019/086536
§ 371 (c)(1),
(2) Date: Jul. 16, 2021

(87) PCT Pub. No.: WO2020/147221
PCT Pub. Date: Jul. 23, 2020

(65) Prior Publication Data
US 2022/0117631 A1 Apr. 21, 2022
US 2022/0117631 A1 Apr. 21, 2022

(30) Foreign Application Priority Data
Jan. 17, 2019 (CN) .......................... 201910043178.7

(51) Int. Cl.
*A61M 1/00* (2006.01)
*A61B 1/07* (2006.01)
*A61B 17/46* (2006.01)

(52) U.S. Cl.
CPC ................ *A61B 17/46* (2013.01); *A61B 1/07* (2013.01); *A61M 1/85* (2021.05); *A61M 1/87* (2021.05)

(58) Field of Classification Search
CPC ....... A61B 1/00105; A61B 1/00; A61B 1/307; A61B 17/42; A61B 17/4241;
(Continued)

(56) References Cited

U.S. PATENT DOCUMENTS

2008/0103357 A1\* 5/2008 Zeiner ................ A61B 1/00087
600/129
2018/0184892 A1 7/2018 Truckai et al.

FOREIGN PATENT DOCUMENTS

CN 2829646 Y 10/2006
CN 201179098 Y 1/2009
(Continued)

OTHER PUBLICATIONS

Int'l Search Report for PCT/CN2019/086536, dated Oct. 18, 2019.

*Primary Examiner* — Erich G Herbermann
*Assistant Examiner* — Linnae E. Raymond
(74) *Attorney, Agent, or Firm* — MaxGoLaw PLLC (57) ABSTRACT

A visualized surgical assembly is provided, characterized in that the visualized surgical assembly includes a disposable drainage tube and a functional tube for providing visualization function, the disposable drainage tube and the functional tube are connected detachable along the axial of the tube body, and the functional tube is provided with a self-destructive part for cutting the disposable drainage tube. A corresponding endoscope is also provided. The visualized (Continued)

surgical assembly is a combination structure of the disposable drainage tube and the functional tube which can provide visualization function. The disposable drainage tube can removable connect with the functional tube, and the functional tube can be repeated disinfection, which can reduce the cost and avoid the risk of cross infection.

13 Claims, 7 Drawing Sheets

(58) Field of Classification Search
CPC ........ A61B 1/00062; A61B 1/303–317; A61B 1/000135; A61B 1/0014; A61B 1/00142; A61B 1/044; A61M 1/86
See application file for complete search history.

(56) References Cited

FOREIGN PATENT DOCUMENTS

| | | | | |
|---|---|---|---|---|
| CN | 201537124 U | | 8/2010 | |
| CN | 201683993 U | | 12/2010 | |
| CN | 103816603 A | * | 5/2014 | .............. A61M 1/85 |
| CN | 203829018 U | | 9/2014 | |
| CN | 104548314 A | | 4/2015 | |
| CN | 205031343 U | | 2/2016 | |
| CN | 105999441 A | * | 10/2016 | |
| CN | 107951549 A | * | 4/2018 | |
| CN | 109498131 A | | 3/2019 | |
| CN | 112370586 A | * | 2/2021 | .............. A61M 1/85 |
| EP | 1284120 A1 | * | 2/2003 | ......... A61B 1/00073 |

* cited by examiner

VISUALIZED SURGICAL ASSEMBLY AND CORRESPONDING ENDOSCOPE THEREOF

CROSS REFERENCE OF RELATED APPLICATIONS

The present application claims the priority of the Chinese invention patent application which application number is 201910043178.7 on Jan. 17, 2019, and the content is incorporated into this application by reference.

FIELD OF THE INVENTION

The invention relates to the medical device field, and further relates to the visual medical device field, in particular to a visualized surgical assembly and corresponding endoscope for abortion.

BACKGROUND

In the clinical operation of visual abortion, it is necessary to use a visual endoscope to observe, locate and aspirate early embryos. In the early abortion operation, due to the difficulty of visualization, it is basically a metal tube with a channel connected to a suction device at the back end to suck out the surface mucosa of the uterine body in the uterine cavity to achieve the suspension of the embryo and the continued conception. Due to the inability to accurately locate the embryo in the uterine cavity, a total suction operation of the inner surface of the uterine cavity is generally performed, but the damage to the non-embryonic mucosal layer cannot be controlled in this way. With the continuous development of technology, embryo positioning under B-ultrasound visits has gradually appeared, which makes the visual operation of positioning and aspirating embryos more advanced than the aborted operation under blind vision. In the later stage, ultra-fine optical fibers appeared, which directly positioned the embryos and performed direct aspiration operations. Recently, the use of photoelectric conversion devices with sensors has made great progress in visualization and more accurate embryo positioning. The above-mentioned methods have achieved a certain degree of visual abortion of abortion, with a certain degree of accurate positioning of embryos and complete abortion success rate.

Under normal circumstances, the drainage tube used in embryo abortion can be made of metal or plastic. The metal pipe fittings can be sterilized and used repeatedly. At present, plastic products with cameras are widely used, which can only be used for one time, which basically meets the requirement of sucking out the embryo after observing the position of the embryo at close range. The operation method is to suck out the embryo in the form of negative pressure to achieve the purpose of suspending the conception.

In clinical medicine, in order to avoid possible medical disputes or other potential pathological conditions, it is necessary to observe the cavity after the abortion operation, including the confirmation of the mucosal layer and the confirmation of the deep body layer, and pass after the operation Using the combination of a fluid perfusion device and a visual flow endoscope, the negative pressure method is changed to the working principle of the uterine dilation type, and the result of the operation is confirmed by observation and observation after the operation, which can protect the patient to the greatest extent. Unnecessary excessive surgery, or discovery of other pathological conditions, inform patients, suggest treatment plans, etc., so as to avoid medical disputes.

Since the existing visual flow endoscope can only meet the requirements of using a drainage tube to suck and remove the embryo after observing the positioning of the embryo, such products have no special requirements for the high resolution of the visual image sensor and the distance of light. However, as medical staff need to observe the internal appearance of the cavity after the operation, after the implementation of the suspension, the ability to infuse the fluid to promote the uterine cavity to expand and leave space to observe the internal condition of the cavity requires high brightness and high brightness. The new visual flow endoscope product with high resolution meets the new clinical needs of medical staff, so the technical invention content of this product fully meets the new clinical applications.

SUMMARY OF THE INVENTION

The object of the present invention is to overcome the drawbacks of the prior arts, to provide a combined visualized surgical assembly with simple operation, accurate positioning, low damage and reduction of medical disputes.

In order to achieve the above purpose, the visualized surgical assembly according to the present invention is as follows:

A visualized surgical assembly comprising a disposable drainage tube and a functional tube for providing visualization function, the disposable drainage tube and the functional tube are connected detachable along the axial of the tube body, and the functional tube is provided with a self-destructive part for cutting the disposable drainage tube.

Preferably, the tube body of the disposable drainage tube and the tube body of the functional tube are detachably connected through a sliding chute-slider combination.

Preferably, the sliding chute-slider combination comprising a sliding chute with an opening arranged along the axial direction of the tube body and a slider matched with the sliding chute, the sliding chute is arranged in one of the disposable drainage tube or functional tube, the slider is arranged on another of the disposable drainage tube or the functional tube, and the coordination of the sliding chute and the slider makes the disposable drainage tube slidable relative to the functional tube along the axial direction of the tube body.

Preferably, the sliding chute comprising a first sliding chute, and the sliding comprising a first slider matched with the first sliding chute, and the first sliding chute has the opening containment cavity which extending outward from the tube body, the first slider is arranged to protrude outwards from the tube body and is accommodated in the containment cavity through the opening.

Preferably, the sliding chute comprising a second sliding chute, the sliding comprising a second sliding matched with the second sliding chute, and the concave tube wall of the tube body where the second sliding chute is located forms the second sliding chute, and the convex tube wall of the tube body where the second slider is located forms the second sliding block.

Preferably, the functional tube comprising a first end and a second end, the first end of the functional tube is provided with a visualization head, and the visualization head includes a transparent mask, a photoelectric conversion module in the transparent mask and a light source in the transparent mask, the tube body of the function tube is provided with an lighting fiber connected with the light source and a cable connected with the photoelectric conversion module, the second end of the function tube is provided with a first handle, and the first handle is provided with a first interface for accessing the lighting fiber and a second interface for connecting the cable.

Preferably, the visualization head is provided with the self-destructive part, and the self-destructive part comprising a positioning pin arranged along the axial direction of the functional tube and a cutting piece arranged on the positioning pin, which is used to locate the end of the disposable drainage tube and cut the disposable drainage tube.

Preferably, the disposable drainage tube comprising a third end and a fourth end, the third end of the disposable drainage tube is correspondingly arranged with the first end of the functional tube, and the fourth end of the disposable drainage tube is arranged correspondingly with the second end of the functional tube, the fourth end of the disposable drainage tube is provided with a second handle matched with the first handle, and the second handle comprising a liquid outlet and a third interface for attracting the suction accessories.

Preferably, the suction accessory comprising a perfusion valve body, one end of the perfusion valve body is connected with a connecting tube for inserting into the disposable drainage tube, and a fastener connected with the third interface, and another end of the perfusion valve body is connected with a suction port with a check-valve, and a liquid inlet is arranged on the side of the perfusion valve body.

Preferably, the first handle is provided with a locating ring for trapping the second handle, and the second handle is provided with a groove for matching with the locating ring.

Preferably, the visualization head comprising an area with the maximum transverse diameter corresponding to the maximum diameter of the combined tube body of the disposable drainage tube and the functional tube, and the end surface of the third end of the disposable drainage tube is a curved end face, the visualization head is provided with a matching surface matched with the curved end face, and the third end of the disposable drainage tube is provided with a side opening.

The invention also provides an endoscope, wherein the corresponding endoscope comprising a visualized surgical assembly according to the visualized surgical assembly.

The visualized surgical assembly of the present invention is a combination structure of the disposable drainage tube and the functional tube which can provide visualization function. The disposable drainage tube is detachably connected with the functional tube, and the functional tube can be repeated disinfection, which can reduce the cost and avoid the risk of cross infection.

Figure 1:
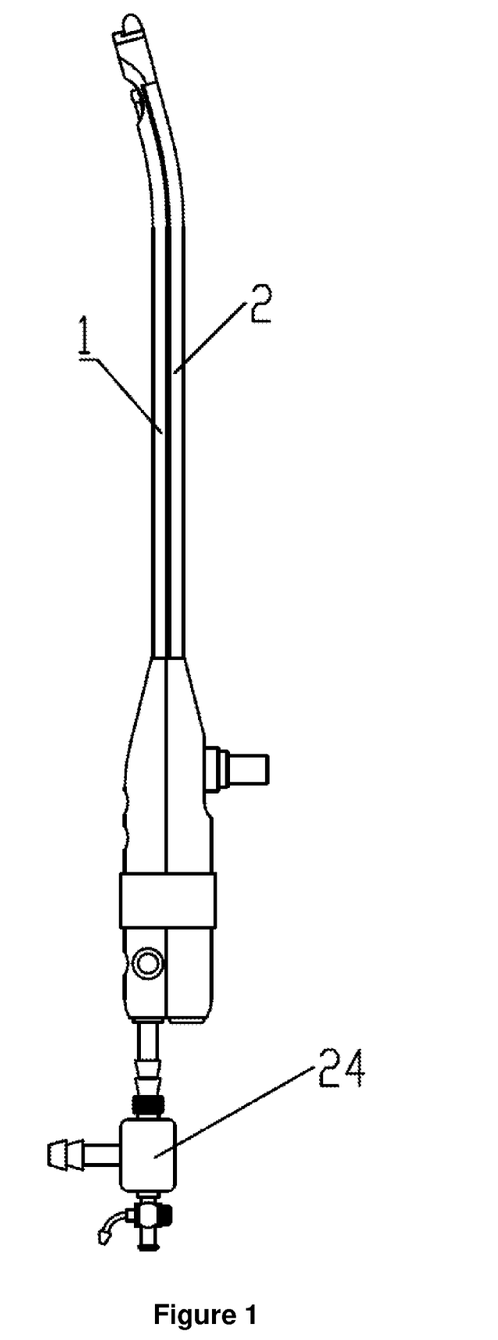
FIG. 1 shows an overall structure diagram of the visualized surgical assembly according to the present invention.

REFERENCE NUMBERS IN FIGURES 1 disposable drainage tube
2 functional tube
3 self-destructive part
4 first sliding chute
5 first slider
6 containment cavity
7 opening
8 second sliding chute
9 second slider
10 visualization head
11 transparent mask
12 photoelectric conversion module
13 light source
14 lighting fiber
15 cable
16 first handle
17 first interface
18 second interface
19 positioning pin
20 cutting piece
21 second handle
22 liquid outlet
23 third interface
24 perfusion valve body
25 connecting tube
26 fastener
27 check-valve
28 suction port
29 liquid inlet
30 locating ring
31 groove
32 curved end face
33 matching surface
34 side opening

DETAILED DESCRIPTION

In order to be able to understand the technical content of the present invention more clearly, the following embodiments are specifically described.

As shown in FIGS. 1 to 8, an embodiment of a visualized surgical assembly provided for the present invention includes a disposable drainage tube 1 and a functional tube 2 for providing visualization function. The disposable drainage tube and the functional tube are detachably connected along the axial direction of the tube body. The functional tube is provided with a self-destructive part 3 for cutting the disposable drainage tube.

The assembly provided by the invention is preferably used for abortion surgery. All parts need to be disinfected before use. The functional tube can use steel structure, which can be reused after repeated disinfection. The disposable drainage tube is a disposable consumable part, which can be used only after being sterilized by high pressure in advance and meeting the requirements of medical specifications, The disposable drainage tube can be cut off when the disposable drainage tube is separated from the functional tube by setting the self-destructive part, so as to prevent the disposable drainage tube from being used again due to negligence.

In the visualized surgical assembly provided by the present invention, the tube body of the disposable drainage tube and the tube body of the functional tube are detachably connected through a sliding chute-slider combination, and the sliding chute-slider combination comprises a sliding chute with an opening arranged along the axial direction of the tube body and a slider matched with the sliding chute. The sliding chute is arranged in one of the disposable drainage tube or functional tube, and the slider is arranged in the other one of the disposable drainage tubes or functional tubes. The coordination of the sliding chute and the slider enables the disposable drainage tube to slide relative to the functional tube along the axial direction of the tube body.

Figure 2:
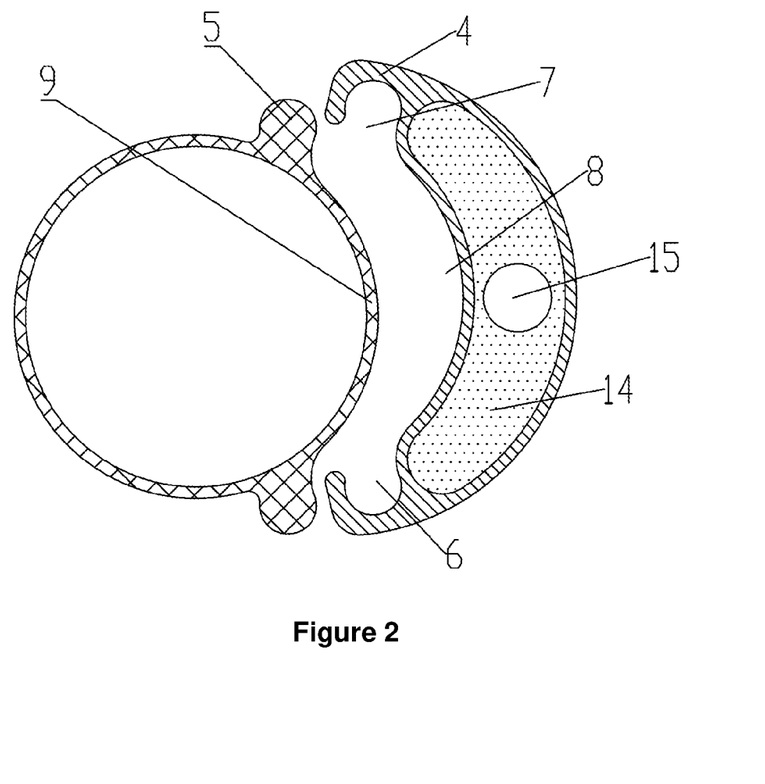
FIG. 2 shows a cross-sectional view of the disposable drainage tube and the functional tube in the visualized surgical assembly according to the present invention.

As shown in FIG. 2, the invention provides a specific embodiment with a sliding chute-slider combination, wherein the disposable drainage tube and the functional tube include two groups of sliding chute-slider combinations for positioning. The first group of sliding chute-slider combination is the first chute 4 and the first slider 5. The first chute 4 is matched with the first slider 5 in size and contour lamp, the first chute has a containment cavity 6 extending outwards from the tube body to form an opening, and the first slider is arranged to protrude outwards from the tube body and is accommodated in the containment cavity through the opening 7.

As shown in FIG. 2, the second group of sliding chute-slider combination includes a second chute 8 and a second slider 9, the concave tube wall of the functional tube forms the second sliding chute, and the convex tube wall of the disposable drainage tube forms the second slider, wherein the cross section of the disposable drainage tube is in the shape of a micro ellipse, and the cross section of the functional tube comprises two arcs, wherein the inner arc forms the second sliding chute, guiding the disposable drainage tube into the correct chute.

Figure 3:
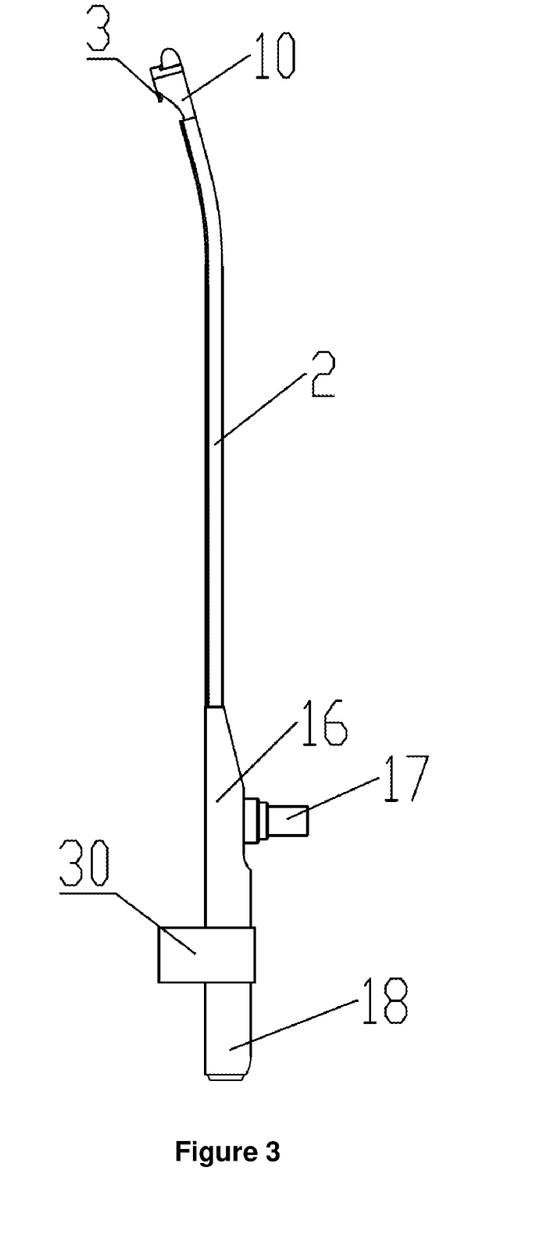
FIG. 3 shows the structural diagram of the functional tube in the visualized surgical assembly according to the present invention.
Figure 4:
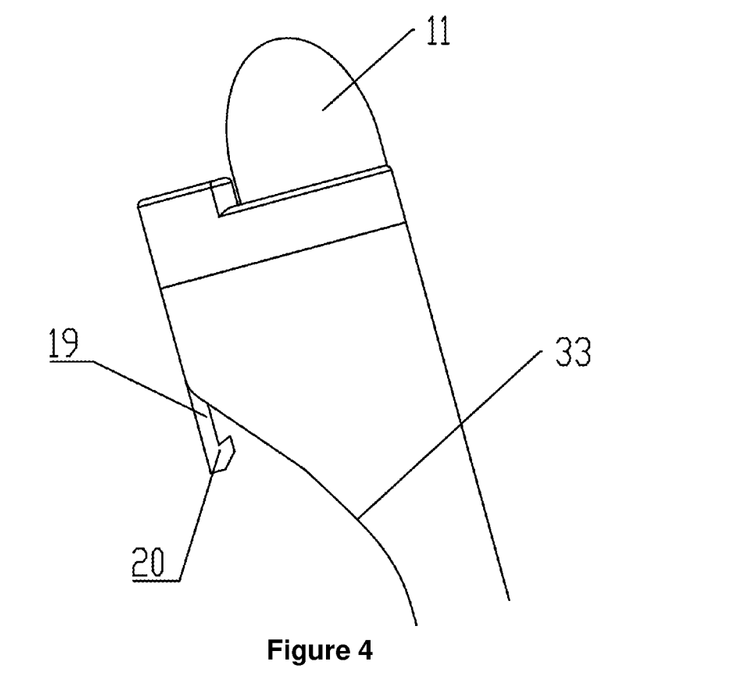
FIG. 4 shows the structural diagram of the visualization head of the functional tube in the visualized surgical assembly according to the present invention.
Figure 5:
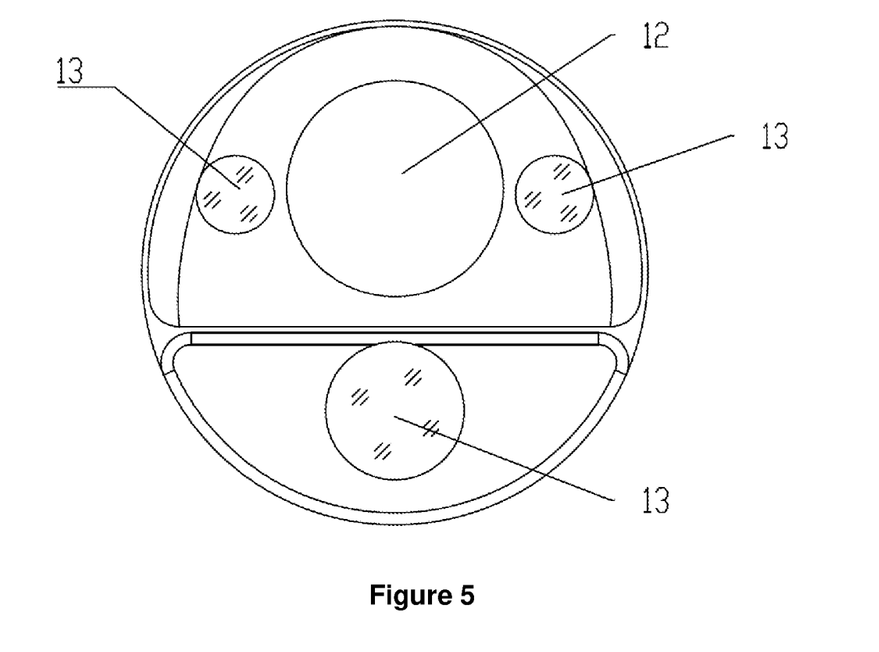
FIG. 5 shows a top diagram of the visualization head of the functional tube in the visualized surgical assembly according to the present invention.

As shown in FIG. 3-5, in a visualized surgical assembly provided by the present invention, the functional tube comprises a first end and a second end. The first end of the functional tube is provided with a visualization head 10. The visualization head includes a transparent mask 11, an photoelectric conversion module 12 in the transparent mask and a light source 13 in the transparent mask, the tube body of the function tube is provided with an lighting fiber 14 connected with the light source and a cable 15 connected with the photoelectric conversion module (as shown in FIG. 2). The second end of the function tube is provided with a first handle 16, and the first handle is provided with a first interface 17 for connecting the lighting fiber and a second interface 18 for connecting the cable.

Among them, the first interface 17 is the connection port used to lead in the light source. Through the lighting fiber built in the function tube, the required light source is transmitted in the visualization head. The first interface is a fast interface, which is convenient for connection and removal, and convenient for disinfection of the function tube.

Among them, the second interface 18 is a quick connector for cable connection. By connecting the cable, the photoelectric signal received by the photoelectric sensor of the visualization head can be accurately displayed through the cable after electronic processing. As for the image of the front end, the second interface is set as a fast interface to facilitate connection and removal, which is convenient for disinfection of functional tubes.

As shown in FIG. 5, the function tube provided by the invention comprises a dual lighting system, namely, two groups of short-range lighting sources and a group of long-distance lighting sources. The photoelectric conversion module generally includes a photoelectric conversion sensor (CMOS) with an imaging objective in the front end.

As shown in FIG. 3-4, in a visualized surgical assembly provided by the invention, the visualization head is provided with the self-destructive part, and the self-destructive part includes a positioning pin 19 arranged along the axial direction of the functional tube and a cutting piece 20 arranged on the positioning pin, which are used to locate the end of the disposable drainage tube and cut the disposable drainage tube. In the process of pulling out the disposable drainage tube, the wall surface of the disposable drainage tube can be cut through by the force of the positioning pin with the reverse inclined mouth (cutting piece), so as to achieve the self-destruction function and avoid the risk of mutual infection caused by the repeated use of the disposable drainage tube.

Figure 6:
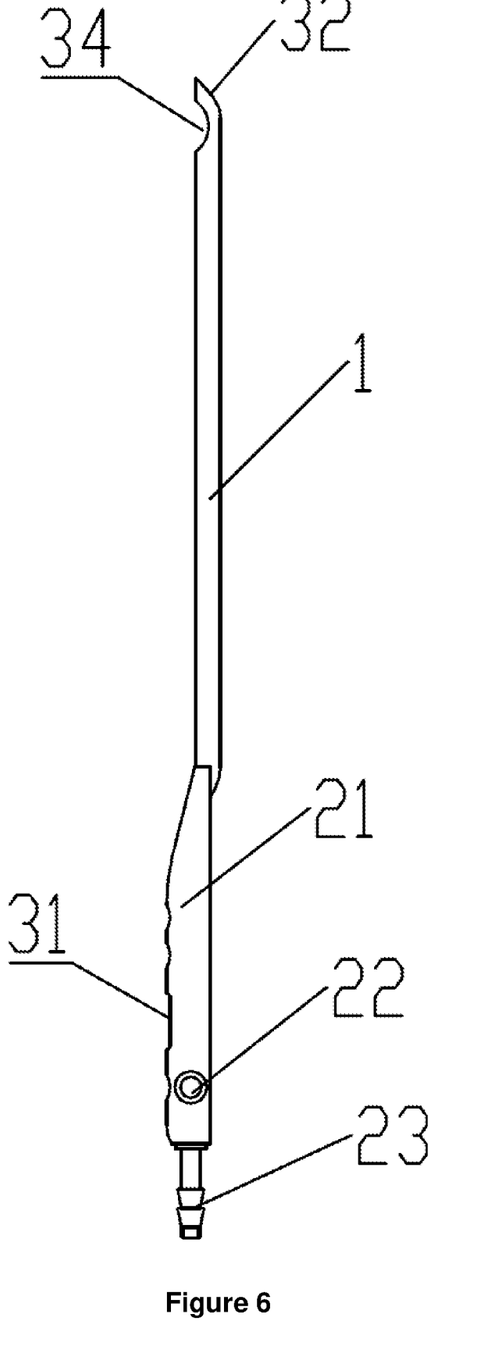
FIG. 6 shows the structural diagram of disposable drainage tube in the visualized surgical assembly according to the present invention.

As shown in FIG. 6, in a visualized surgical assembly provided by the present invention, the disposable drainage tube includes a third end and a fourth end, the third end of the disposable drainage tube is correspondingly arranged with the first end of the functional tube, and the fourth end of the disposable drainage tube is arranged correspondingly with the second end of the functional tube, The fourth end of the disposable drainage tube is provided with a second handle 21 matched with the first handle. The second handle comprises a liquid outlet 22 and a third interface 23 for connecting with the suction accessories. Among them, the third interface 23 is a fast interface in the shape of a pagoda shaped as a triangle, which is convenient for quick connection and removal in the process of use.

Figure 8:
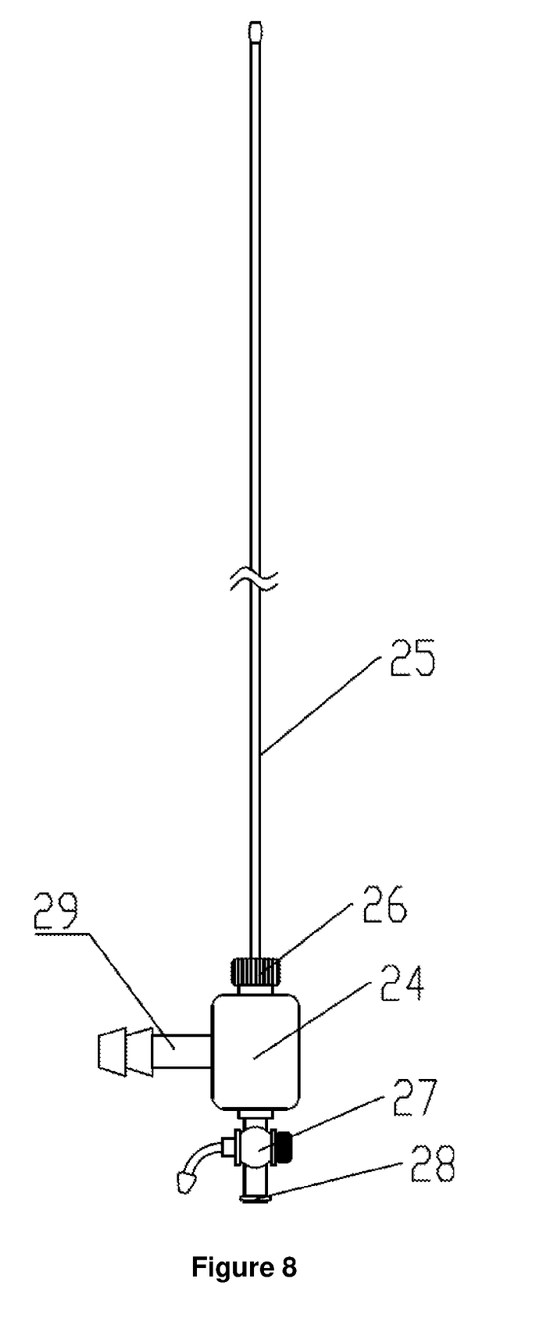
FIG. 8 shows the structural diagram of the suction accessories in the visualized surgical assembly according to the present invention.

As shown in FIG. 8, in a visualized surgical assembly provided by the present invention, the suction accessory comprises a perfusion valve body 24, one end of the perfusion valve body is connected with a connecting tube 25 for inserting into the disposable drainage tube, and a fastener 26 connected with the third interface is arranged, and the other end of the perfusion valve body is connected with the suction port 28 of the check valve 27, The side surface of the perfusion valve body is provided with a liquid inlet 29, and the head of the connecting tube 25 is also provided with a connecting fixed head. The fastener 26 can use speed nuts, etc.

As shown in FIG. 1, in order to install the suction accessories, disposable drainage tubes and functional tubes, the suction accessories are fixed on the disposable drainage tubes through the fasteners 26 and the third interface 23, and the disposable drainage tubes and functional tubes are detachably connected through the sliding chute slider combination, the locating ring groove assembly, the arc end face fitting surface and the self-destructive parts. The assembly has the functions of visualization, attraction and illumination.

Figure 7:
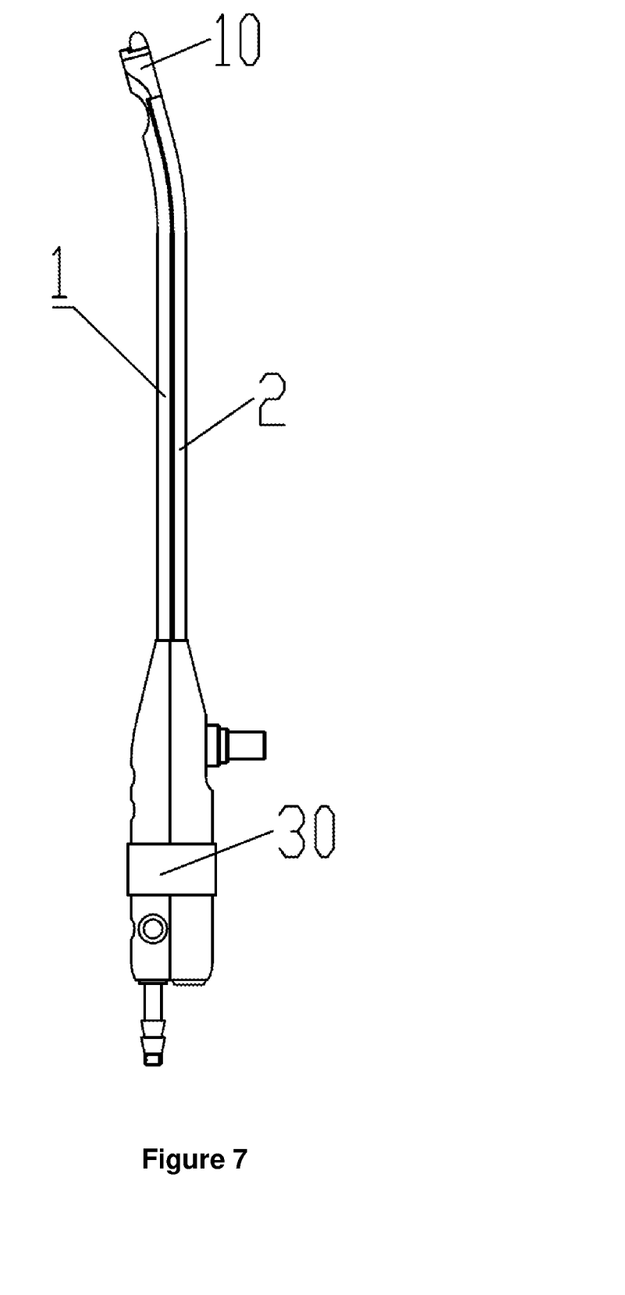
FIG. 7 shows the combined schematic diagram of disposable drainage tube and functional tube in the visualized surgical assembly according to the present invention.

As shown in FIG. 3, 6-7, in a visualized surgical assembly provided by the present invention, the first handle is provided with a locating ring 30 for covering the second handle, and the second handle is provided with a groove 31 for matching with the locating ring. The locating ring is used to guide and locate the combination of disposable drainage tube and functional tube. After the disposable drainage tube reaches the top and coincides with the head position of the functional tube, the fixed groove of the disposable drainage tube just fits with the locating ring guide piece of the functional tube.

In addition, as shown in FIG. 6, the surface of the second handle is also provided with a dent which is convenient for holding.

As shown in FIGS. 4, 6-7, in the visualized surgical assembly provided by the invention, the visualization head has an area with the maximum transverse diameter corresponding to the maximum diameter of the combined tube body of the disposable drainage tube and the functional tube, and the end surface of the third end of the disposable drainage tube is a curved end face 32. The visualization head is provided with a matching surface 33 matched with the curved end face, and the third end of the disposable drainage tube is provided with a side opening 34, wherein the side opening is preferably arranged as an oval side opening, which is used for sucking out the embryo without tissue need.

The invention also provides an endoscope, wherein the endoscope comprises the visualized operation assembly. Preferably, the endoscope is a rigid visible abortion mirror. Among them, the disposable drainage tube is combined with the functional tube to connect the functional tube with the display screen, and the video image of the photoelectric signal received by the sensor can be observed, which an extended endoscope is.

The visualized surgical assembly of the present invention is a combination structure of the disposable drainage tube and the functional tube which can provide visualization function.

The disposable drainage tube is detachably connected with the functional tube, and the functional tube can be repeated disinfection, which can reduce the cost and avoid the risk of cross infection.

The invention is worthy of a very clever combination of design concepts, the possible risks from the design to achieve prevention. Through the expansion method, it has replaced some functions of hysteroscopy, reduced the possibility of medical disputes, and brought a new way of reform for new medical minimally invasive surgery, which is a very forward-looking innovative design, and will be used in a wide range of medical units at different levels.

The visual surgery assembly provided by the invention is an ideal product with simple operation, small trauma, accurate positioning, low damage degree, fast healing and reducing medical disputes.

In this specification, the present invention has been described with reference to its specific embodiments. However, it is clear that various modifications and changes can still be made without departing from the spirit and scope of the present invention. Therefore, the description and drawings should be regarded as illustrative rather than restrictive.

The invention claimed is:

1. A surgical assembly for visualizing, said surgical assembly comprising a disposable drainage tube and a functional tube for providing visualization function, the disposable drainage tube and the functional tube detachably connected along an axial direction of a tube body of the disposable drainage tube and a tube body of the functional tube, and the functional tube is provided with a self-destructive part for cutting the disposable drainage tube.

2. The surgical assembly according to claim 1, wherein the tube body of the disposable drainage tube and the tube body of the functional tube are detachably connected through a sliding chute-slider combination.

3. The surgical assembly according to claim 2, wherein the sliding chute-slider combination comprises a sliding chute with an opening arranged along the axial direction of the tube bodies and a slider matched with the sliding chute, the sliding chute is arranged in one of the disposable drainage tube or the functional tube, the slider arranged on another of the disposable drainage tube or the functional tube, and the coordination of the sliding chute and the slider makes the disposable drainage tube slidable relative to the functional tube along the axial direction of the tube bodies.

4. The surgical assembly according to claim 3, wherein the sliding chute comprises a first sliding chute, and the slider comprises a first slider matched with the first sliding chute, and the first sliding chute has an opening containment cavity which extends outward from the tube body of one of the disposable drainage tube or the functional tube, the first slider is arranged to protrude outwards from the tube body of one of the disposable drainage tube or the functional tube and is accommodated in the containment cavity through the opening.

5. The surgical assembly according to claim 4, wherein the sliding chute comprises a second sliding chute, the slider comprises a second slider matched with the second sliding chute, and a concave tube wall of the tube body of one of the disposable drainage tube or functional tube where the second sliding chute is located forms the second sliding chute, and a convex tube wall of the tube body of the other of the disposable drainage tube or functional tube where the second slider is located forms the second slider.

6. The surgical assembly according to claim 3, wherein the sliding chute comprises a second sliding chute, the slider comprises a second slider matched with the second sliding chute, and a concave tube wall of the tube body of one of the disposable drainage tube or functional tube where the second sliding chute is located forms the second sliding chute, and a convex tube wall of the tube body of the other of the disposable drainage tube or functional tube where the second slider is located forms the second slider.

7. The surgical assembly according to claim 1, wherein the functional tube comprises a first end and a second end, the first end of the functional tube is provided with a visualization head, and the visualization head includes a transparent mask, a photoelectric conversion module in the transparent mask and a light source in the transparent mask, the tube body of the functional tube is provided with a lighting fiber connected with the light source and a cable connected with the photoelectric conversion module, the second end of the functional tube is provided with a first handle, and the first handle is provided with a first interface for accessing the lighting fiber and a second interface for connecting the cable.

8. The surgical assembly according to claim 7, wherein the visualization head is provided with the self-destructive part, and the self-destructive part comprises a positioning pin arranged along the axial direction of the functional tube and a cutting piece is arranged on the positioning pin, which is used to locate the end of the disposable drainage tube and cut the disposable drainage tube.

9. The surgical assembly according to claim 8, wherein the disposable drainage tube comprises a third end and a fourth end, the third end of the disposable drainage tube is correspondingly arranged with the first end of the functional tube, and the fourth end of the disposable drainage tube is arranged correspondingly with the second end of the functional tube, the fourth end of the disposable drainage tube is provided with a second handle matched with the first handle, and the second handle comprises a liquid outlet and a third interface for attracting a suction accessory.

10. The surgical assembly according to claim 9, wherein the first handle is provided with a locating ring for trapping the second handle, and the second handle is provided with a groove for matching with the locating ring.

11. The surgical assembly according to claim 9, wherein the visualization head comprises an area with the maximum transverse diameter corresponding to the maximum diameter of the combined tube body of the disposable drainage tube and the functional tube, and the end surface of the third end of the disposable drainage tube is a curved end face, the visualization head is provided with a matching surface matched with the curved end face, and the third end of the disposable drainage tube is provided with a side opening.

12. The surgical assembly according to claim 9, wherein the suction accessory comprises a perfusion valve body, one end of the perfusion valve body is connected with a connecting tube for inserting into the disposable drainage tube, and a fastener connected with the third interface, and another end of the perfusion valve body is connected with a suction port with a check-valve, and a liquid inlet is arranged on the side of the perfusion valve body.

13. An endoscope, wherein the endoscope comprises a surgical assembly according to claim 1.

\* \* \* \* \*